United States Patent
Reichert et al.

(10) Patent No.: US 9,617,209 B2
(45) Date of Patent: Apr. 11, 2017

(54) PROCESS FOR OBTAINING METHIONINE

(71) Applicants: Stefan Reichert, Frankfurt (DE); Harald Jakob, Hasselroth (DE); Hans Joachim Hasselbach, Gelnhausen (DE); Martin Koerfer, Kahl (DE)

(72) Inventors: Stefan Reichert, Frankfurt (DE); Harald Jakob, Hasselroth (DE); Hans Joachim Hasselbach, Gelnhausen (DE); Martin Koerfer, Kahl (DE)

(73) Assignee: EVONIK DEGUSSA GmbH, Essen (DE)

( * ) Notice: Subject to any disclaimer, the term of this patent is extended or adjusted under 35 U.S.C. 154(b) by 0 days.

(21) Appl. No.: 15/021,541

(22) PCT Filed: Sep. 10, 2014

(86) PCT No.: PCT/EP2014/069247
§ 371 (c)(1),
(2) Date: Mar. 11, 2016

(87) PCT Pub. No.: WO2015/039935
PCT Pub. Date: Mar. 26, 2015

(65) Prior Publication Data
US 2016/0229799 A1    Aug. 11, 2016

(30) Foreign Application Priority Data

Sep. 17, 2013 (EP) .................................... 13184831

(51) Int. Cl.
*C07C 321/14* (2006.01)
*C07C 319/20* (2006.01)
*C07C 319/26* (2006.01)
*C07C 319/28* (2006.01)

(52) U.S. Cl.
CPC .......... *C07C 321/14* (2013.01); *C07C 319/20* (2013.01); *C07C 319/26* (2013.01); *C07C 319/28* (2013.01); *C07B 2200/13* (2013.01)

(58) Field of Classification Search
CPC ... C07C 321/14; C07C 319/20; C07C 319/26; C07C 319/28

USPC ......................................................... 562/559
See application file for complete search history.

(56) References Cited

U.S. PATENT DOCUMENTS

| | | | |
|---|---|---|---|
| 5,770,769 A | 6/1998 | Geiger et al. |
| 5,990,349 A | 11/1999 | Geiger et al. |
| 6,287,627 B1 | 9/2001 | Binder et al. |
| 6,797,827 B2 | 9/2004 | Koerfer et al. |
| 7,119,228 B2 | 10/2006 | Buss et al. |
| 7,179,938 B2 | 2/2007 | Weckbecker et al. |
| 9,023,284 B2 | 5/2015 | Hasselbach et al. |
| 9,029,597 B2 | 5/2015 | Steffan et al. |
| 9,156,782 B2 | 10/2015 | Koerfer et al. |
| 2005/0131111 A1 | 6/2005 | Weckbecker et al. |
| 2005/0176115 A1 | 8/2005 | Kobayashi et al. |

FOREIGN PATENT DOCUMENTS

| | | |
|---|---|---|
| JP | 46-019610 B | 6/1971 |
| JP | 11-158140 A | 6/1999 |
| WO | 03/050071 A1 | 6/2003 |

OTHER PUBLICATIONS

International Search Report Issued Nov. 28, 2014, in PCT/EP2014/069247 Filed Sep. 10, 2014.
"Dl-methionine crystallization," WPI/Thomson, vol. 1971, No. 21, Jan. 1, 1971, XP002681651 (1 page).
Canselier, et al., "The Effects of Surfactants on Crystallization Phenomena," Journal of Dispersion Science and Technology, vol. 14, No. 6, Jan. 1993, XP008011857 (20 pages).
U.S. Appl. No. 14/638,870, filed Mar. 4, 2015, Hasselbach, et al.
U.S. Appl. No. 14/850,207, filed Sep. 10, 2015, Koerfer, et al.
U.S. Appl. No. 15/022,642, filed Mar. 17, 2016, Alt, et al.

*Primary Examiner* — Yevegeny Valenrod
(74) *Attorney, Agent, or Firm* — Oblon, McClelland, Maier & Neustadt, L.L.P.

(57) ABSTRACT

The invention relates to a method for crystallizing D,L-methionine from aqueous solutions and/or suspensions containing D,L-methionine and D,L-methionine ammonium salts, having a Met content of 70-180 g/kg, an $NH_4^+$ content of 1-5 g/kg, in the presence of a crystallization additive, which comprises a nonionic or anionic surfactant or a mixture of various nonionic or anionic surfactants, in which the temperature of the solution and/or suspension is lowered directly or stepwise from $T_1=85-110°$ C. to $T_2=30-50°$ C., so that D,L-methionine precipitates as a solid.

22 Claims, 1 Drawing Sheet

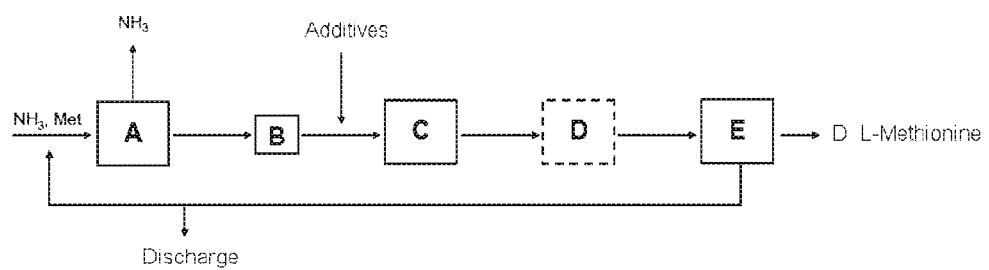

PROCESS FOR OBTAINING METHIONINE

The invention provides a method for isolating D,L-methionine with bulk densities>550 g/l from solutions containing D,L-methionine ammonium salt.

PRIOR ART

Methods for producing D,L-methionine are known in which the D,L-methionine is initially obtained as ammonium methioninate.

According to US20050176115, an aqueous, ammonium-containing D,L-methionine solution is obtained by reacting aqueous solutions of 2-amino-4-methylthiobutyronitrile already in the presence of $NH_3$ using biocatalysts to give D,L-methionine. The D,L-methionine is then precipitated by removing the ammonia under reduced pressure. The D,L-methionine thus obtained has a purity of 99%. The bulk density of the D,L-methionine obtained is not stated.

Likewise in JP2004-254690. D,L-methionine and $NH_3$ are formed by reacting 2-amino-4-methylthiobutyronitrile with a biocatalyst. The solubility of the methionine is increased by the presence of ammonia which facilitates the removal of the biocatalyst. The exact isolation conditions and the product properties of the D,L-methionine are not stated in JP2004-254690.

DE 60127538 describes a method in which D,L-methionine is produced from methionine amide by a catalyzed saponification reaction. Here the ammonia is completely removed from the resulting ammonium methioninate solution by stripping and the methionine is crystallised out, although the bulk densities of the methionine obtained are not stated.

In WO 2008006977, D,L-methionine is obtained from methionine hydantoin by saponification with $NH_3$ and the D,L-methionine is obtained by evaporation of $NH_3$ and $CO_2$ under reduced pressure. Nothing is stated concerning the product properties.

WO2007034065 also describes an ammoniacal saponification of methionine hydantoin. The ammonia is removed from the ammonium methioninate solution in a stripping column and the methionine is subsequently precipitated by cooling the solution. The product properties of the methionine formed are not mentioned therein. DE 10238212 describes a method in which methionine hydantoin is saponified in water at high temperatures with or without catalyst. $NH_3$ and $CO_2$ are partially removed before crystallization of the resulting methionine. No mention is made of the residual amounts of $CO_2$ and ammonia in the solution from which the crystallization takes place, nor is anything revealed concerning the bulk density of the resulting methionine.

WO 2003050071 describes aqueous mixtures of fatty acid polyethylene glycol esters with modified celluloses, which are used as auxiliaries in the crystallization of methionine from potassium methioninate solutions neutralized with carbon dioxide from the alkaline saponification of methionine hydantoin. In these particular methods in the presence of large amounts of potassium, bulk densities of up to 586 g/l are obtained, in one case of 620 g/l (with hydroxyethylcellulose additive). No details are given, however, for crystallization of D,L-methionine from solutions containing D,L-ammonium methioninate.

The solubility of D,L-methionine is increased in the presence of $NH_3$ (see solubility curves from JP2004-254690).

For an economic method for isolating D,L-methionine, it is accordingly advantageous to remove the ammonia as completely as possible in order to maximize the amount of crystallizable D,L-methionine. For this purpose, the ammonia may be removed by various methods known from the literature, such as stripping, evaporation under reduced pressure etc.

BRIEF DESCRIPTION OF THE DRAWINGS

FIG. 1 shows schematically the continuous procedure of the method according to the invention.

OBJECT OF THE INVENTION

The object of the invention is to provide a method for isolating D,L-methionine, starting from solutions containing ammonium methioninate, in which the D,L-methionine is obtained with high bulk densities of >550 g/l.

DESCRIPTION

The present investigations have shown that the D,L-methionine when crystallized from aqueous solutions is typically obtained with low bulk densities of <550 g/l. A significant increase in the bulk density could not be achieved solely by the addition of crystallization additives. Surprisingly, it has been shown that a residual amount of $NH_3$ in combination with added additives results in D,L-methionine with higher bulk density.

Since in aqueous solutions comprising both $NH_3$ and methionine an equilibrium is established between ammonium methioninate on one side and methionine and ammonia on the other side, reference is made only to the $NH_4^+$ concentrations below for simplicity, irrespective of whether this relates to $NH_4^+$ or $NH_3$.

The object mentioned above and also other related but not explicitly stated objects are achieved by the provision of a method for crystallizing D,L-methionine from aqueous solutions and/or suspensions containing D,L-methionine and D,L-methionine ammonium salt, having a Met content (comprising the total methionine in the form of D,L-methionine and D,L-methionine ammonium salt) of 70-180 g/kg of solution and/or suspension (7-18% by weight), preferably 90-150 g/kg (9-15% by weight), an $NH_4^+$ content of 1-5 g/kg of solution and/or suspension (0.1-0.5% by weight), preferably 1.5 to 3.0 g/kg (0.15-0.3% by weight), in the presence of a crystallization additive, which comprises a nonionic or anionic surfactant or a mixture of various nonionic or anionic surfactants, in which the temperature of the solution and/or suspension is lowered directly or stepwise from a temperature range of $T_1$=85-110° C. to a temperature range of $T_2$=30-50° C., so that methionine precipitates as a solid from the solution and/or suspension.

Aqueous solution containing D,L-methionine and D,L-methionine ammonium salt is understood to mean here that the predominant proportion of the total methionine (Met) present is dissolved and only low Met proportions of max, 5% are present undissolved, i.e. suspended.

Aqueous suspension containing D,L-methionine and D,L-methionine ammonium salt is understood to mean here that a significant proportion, namely of >5%, of the total methionine present is suspended, while the remainder is present in dissolved form.

Correspondingly, the optimal $NH_4+$ concentration, based on methionine, is at least ca. 5 g $NH_4^+$/kg Met and not more than ca. 60 g NH$_4^+$/kg Met, when the methionine concentration in the solution is in the range of 90 g/kg to 150 g/kg.

The NH$_4^+$ concentration may in this case be determined, for example, using an NH$_4^+$-sensitive electrode according to known methods. The NH$_4^+$ concentration is generally determined in this case by measurement on a sample solution adjusted to pH 11 and comparing with the measurement on NH$_4$Cl solutions of known concentration also adjusted to pH 11.

The methionine concentration in the solution and/or suspension is most easily determined by HPLC.

By means of the combination described of the presence of NH$_4^+$ ions, the addition of crystallization additive and the temperature regulation of the crystallization and using the method according to the invention, coarse-grained methionine crystals which may be readily filtered and having a bulk density of >550 g/l after drying are obtained.

Suitable as anionic surfactants are particularly surfactants according to one of the compounds depicted in formulae 1 to 3, or mixtures thereof:

$$R^1\text{—}O\text{—}SO_3M \qquad \text{(formula 1)}$$

$$R^2\text{—}O\text{—}(CH_2)_n\text{—}SO_3M \qquad \text{(formula 2)}$$

$$R^3\text{—}(O\text{—}C_2H_4)_n\text{—}O\text{—}SO_3M \qquad \text{(formula 3)}$$

where n is an integer from 1 to 10, M is sodium or potassium and $R^1$, $R^2$ and $R^3$ are a linear, branched or cyclic, saturated or unsaturated $C_8$- to $C_{20}$-alkyl group or an aryl group. Relatively high bulk densities of 564 to 588 kg/l were obtained with these surfactants, as shown in Table 1 in Example 1 with the additives 2, 3 and 4.

Preference is given to using surfactants in which n equals 2 and $R^1$, $R^2$ and $R^3$ are linear, saturated $C_8$- to $C_{18}$-alkyl groups, since these are readily commercially available and effective.

Particular preference is given to using anionic surfactants of the formulae $C_nH_{2n+1}$—O—$SO_3$Na, where $n=12$ to 18 (Sulfopon® 1218G, Oleochemicals)

$C_nH_{2n+1}$—O—$C_2H_4$—$SO_3$Na, where $n=8$ to 18 (Hostapon® SCI 85, Clariant)

$C_nH_{2n+1}$—$(OC_2H_4)_2$—O—$SO_3$Na, where $n=12$ (Disponil® FES 27, Cognis)

In a preferred embodiment of the method, the nonionic surfactant used is a sorbitan fatty acid ester or a mixture of various sorbitan fatty acid esters, particularly preferably polyethoxylated sorbitan fatty acid esters. Sorbitan fatty acid esters have the advantage that they are effective and readily commercially available. In a very particularly preferred embodiment, the nonionic surfactant is a polyethoxylated sorbitan tristearate according to formula 4:

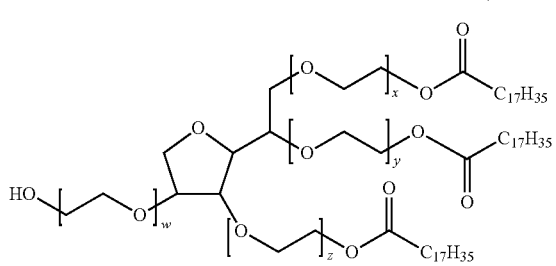

(formula 4)

where w+x+y+z=20.

With these surfactants, a relatively high bulk density of 578 kg/l was obtained, as shown in Example 3.

The concentration of the crystallization additive (based on the active ingredient) in the solution and/or suspension from which the crystallization takes place is preferably at least 700 ppm and not more than 4000 ppm, based on the total mass of the solution and/or suspension, particularly preferably at least 750 ppm and not more than 2000 ppm, most particularly preferably at least 800 ppm and not more than 1000 ppm. This ensures a good development of the additive effect without introducing too many foreign materials into the product solution.

In order to achieve an optimal dosage and distribution of the crystallization additive, the latter is preferably used in the form of an aqueous solution or emulsion, wherein the concentration of the crystallization additive in the solution or emulsion is preferably 2 to 15% by weight.

In a preferred embodiment of the method according to the invention, the solution from which the crystallization takes place additionally comprises a defoamer. The function of the defoamer is to suppress the foam occurring during the handling of the methionine solution and/or suspension and caused or intensified by some of the crystallization additives mentioned above. Moreover, a synergistic effect arises, surprisingly, during simultaneous use of defoamer and crystallization additives in the case of the bulk densities of the methionine achieved, whereby bulk densities of even over 600 g/l are attained and simultaneously the negative effects of enrichment processes are avoided and therefore the method according to the invention can also be carried out in continuous mode. This is particularly apparent by comparing experiments 2, 3 and 4 (without added defoamer→bulk densities of 564-588 kg/l)) with experiments 8, 9 and 10 (with added defoamer→bulk densities of 630-634 kg/l) respectively in Table 1 of Example 1. In addition, this embodiment enables the use of less crystallization additive.

Preference is given to using defoamers comprising silicone oil, since these have proven to be particularly effective, wherein preferably a silicone oil having a kinematic viscosity of 0.65 to 10 000 mm²/s (measured at 25° C. according to DIN 53018), particularly preferably 90 to 1500 mm²/s, is used. The defoamer may furthermore comprise constituents which are effective as emulsifiers, for example mixtures of polyethoxylated fatty acids and polyethoxylated fatty alcohols. The defoamer may likewise comprise silica. In a preferred embodiment, the defoamer is an aqueous solution comprising 5 to 10% by weight silicone oil, 0.05 to 1% by weight silica, 0.5 to 5% by weight of a mixture of polyethoxylated fatty acids, and 2 to 7% by weight of a mixture of polyethoxylated fatty alcohols.

Preference is given to using the defoamer in a mixture with the crystallization additive. In order to achieve a continuous, stable dosage of the defoamer, it is preferably further diluted with water prior to use.

The use of silicone oil defoamers means that silicon may be detected in the methionine produced by the method according to the invention using a suitable analytical method (e.g. X-ray photoelectron spectroscopy, abbreviated to XPS).

Preference is given to using the defoamer in the method according to the invention such that the weight ratio of the defoamer:crystallization additive (based on the active ingredient) in the solution or suspension from which the crystallization takes place, is in the range of 4:1 to 1:1, preferably in the range of 3:1 to 2:1 and the concentration of the crystallization additive (based on the active ingredient) is in this case at least 50 ppm and not more than 1200 ppm, based on the total mass of the solution and/or suspension, preferably 100 ppm to 600 ppm, particularly preferably 200 ppm to 400 ppm. The high D,L-methionine bulk densities achieved in this case of significantly above 600 g/l can be particularly effectively seen in Example 4/Table 3.

The method according to the invention is in this case preferably carried out such that the crystallization takes place by introducing an aqueous solution and/or suspension containing D,L-methionine and D,L-methionine ammonium salt heated to 85 to 110° C. into an aqueous solution and/or suspension containing D,L-methionine and D,L-methionine ammonium salt warmed to 30 to 50° C., wherein the temperature of the resulting mixture is constantly maintained between 30 and 50° C.

Very particular preference is given in this case to introducing an aqueous solution containing D,L-methionine and D,L-methionine ammonium salt heated to 85 to 110° C. into an aqueous suspension containing D,L-methionine and D,L-methionine ammonium salt warmed to 30 to 50° C. This has the advantage that crystals are obtained which may be particularly effectively filtered.

A further preferred embodiment of the method is characterized in that the crystallization is carried out in two stages, wherein, in the first crystallization stage, a solution and/or suspension containing D,L-methionine and D,L-methionine ammonium salt heated to 85 to 110° C. is introduced into a suspension containing D,L-methionine and D,L-methionine ammonium salt warmed to 60 to 80° C. and the temperature of the resulting mixture is constantly maintained between 60 and 80° C. and wherein the suspension containing D,L-methionine and D,L-methionine ammonium salt warmed to 60 to 80° C. obtained in the first crystallization stage is introduced in a second crystallization stage into a suspension containing D,L-methionine and D,L-methionine ammonium salt warmed to 30 to 50° C., wherein the temperature of the resulting mixture is constantly maintained between 30 and 50° C. In this case the proportion of impurities in the crystallization broth can be particularly effectively controlled or can be depleted by discharging at a suitable point, without relinquishing the advantageous effect of the bulk density above 550 g/l.

A furthermore preferred embodiment of the method according to the invention is characterized in that the crystallization is carried out by vacuum crystallization, wherein the pressure in the first crystallization stage is 60 to 1000 mbar and, if a two-stage crystallization is carried out, the pressure in the second crystallization stage is 35 to 200 mbar. This has the advantage that surfaces employed are less cold. Cold surfaces may lead to undesired local caking.

The aqueous solutions and/or suspensions containing D,L-methionine and D,L-methionine ammonium salts used for the crystallization method according to the invention may be prepared beforehand by dissolving and/or suspending D,L-methionine in water in the presence of appropriate amounts of ammonia. The methionine may originate from any manufacturing process which renders the method universally applicable.

It has proven to be advantageous in this case that D,L-methionine having a methionine content of at least 90% by weight, preferably at least 95% by weight, is used for the dissolution.

Particularly suitable for this purpose is D,L-methionine in the form of pure methionine and/or crude methionine from any manufacturing process having a residual moisture of 0.1 to 9.5% by weight, preferably 0.2 to 4.5% by weight. The use of pure or crude methionine of a quality which is still filter-moist from an industrial process for preparing D,L-methionine is advantageous, since in this manner D,L-methionine with the desired properties, particularly the bulk density>550 kg/l, may be obtained directly at the end of the process after drying.

The method according to the invention is also particularly suitable for isolating D,L-methionine from aqueous solutions and/or suspensions containing D,L-methionine and D,L-methionine ammonium salts which have been prepared by hydrolysis of D,L-methionine nitrile and/or D,L-methionine amide, specifically without the use of salt-forming acidic or basic saponification agents (such as HCl, $H_2SO_4$ or alkali metal hydroxides such as NaOH or KOH) other than ammonia. Such non-salt-forming saponification agents or saponification catalysts such as $TiO_2$ or $MnO_2$ are known from the relevant patent literature and, like ammonia as saponfication agent in the saponification of D,L-methionine nitrile and/or D,L-methionine amide, directly yield aqueous solutions and/or suspensions containing D,L-methionine and D,L-methionine ammonium salts from which D,L-methionine may be obtained by crystallization by the method according to the invention. Such aqueous solutions and/or suspensions therefore contain practically no alkali metal ions, such as $Na^+$ or $K^+$ ions.

Accordingly, a further subject of the invention is a method for preparing D,L-methionine, in which an aqueous solution of D,L-methionine ammonium salt is initially formed by hydrolysis of D,L-methionine nitrile and/or D,L-methionine amide, and an aqueous solution and/or suspension containing D,L-methionine and D,L-methionine ammonium salt is produced therefrom by partial removal of the ammonia from the D,L-methionine ammonium salt, which is present therein bound as ammonium ion, from which D,L-methionine is then obtained by the crystallization method according to the invention.

In the method according to the invention, the ammonium methioninate solution primarily formed is therefore initially subjected to ammonia depletion. Methods for this purpose are known: this may be achieved, for example, by heating under reduced pressure or by stripping with steam.

Accordingly, the method according to the invention for preparing D,L-methionine is preferably carried out such that the aqueous solution of D,L-methionine ammonium salt is brought to an $NH_4^+$ content of 1-5 g/kg of the solution and/or suspension, preferably 1.5 to 3.0 g/kg, by evaporating and/or stripping off of ammonia prior to the crystallization, e.g. by heating under reduced pressure or by stripping with steam.

Here, the ammonium concentration in accordance with the invention is only depleted, however, to values in a range of ca. 5 to ca. 60 g $NH_3$/kg of methionine. In this case, it is advantageous to select a temperature sufficiently high such that D,L-methionine does not already precipitate during the removal of ammonia but remains in solution. The hot methionine solution is preferably rapidly cooled down by feeding into a precharged, cooler methionine suspension, whereby an overconcentration of dissolved D,L-methionine is generated and D,L-methionine precipitates from the solution.

A procedure may also be employed here in which the aqueous solution and/or suspension of D,L-methionine and/or D,L-methionine ammonium salt is brought to the appropriate Met content of 70-180 g/kg of the solution, preferably 90 to 150 g/kg of the solution, by addition of water and/or D,L-methionine, which renders the method of variable and flexible use.

The precipitated D,L-methionine is preferably separated from the resulting mother liquor and dried or is initially recrystallized and is dried after separation from the mother liquor obtained in this case, whereupon D,L-methionine with a purity of at least 99% by weight and a bulk density of at least 550 g/l after drying is finally obtained.

The mother liquor obtained here is preferably fed back into a crystallization stage, which results in minimization of losses of methionine.

The method may either be carried out continuously or batchwise.

FIG. 1 shows by way of example and schematically the continuous procedure of the method according to the invention. The ammonium methioninate solution is initially fed into a suitable apparatus A for reduction of the ammonia concentration. This is generally an evaporation system, e.g. comprising a falling-film evaporator or circulation evaporator. The conditions here are selected such that an $NH_3$ amount of 1 to 5 g/kg of the solution and/or suspension is present in the product stream, while the Met concentration is in a range of 70-180 g/kg of the solution and/or suspension, preferably 90-150 g/kg. The crystallization additive according to the invention, optionally including defoamer, is added continuously to this product stream. The temperature of the solution and/or suspension containing D,L-methionine and/or DL-methionine ammonium salt is preferably 90 to 100° C. This Met solution and/or suspension may be heated to 100 to 110° C. if required by means of one or more heat exchangers B and subsequently may be preferably rapidly cooled in one or more stages to temperatures between 30 and 50° C. in a suitable crystallization apparatus C, whereupon the D,L-methionine crystallizes out. If required, the D,L-methionine suspension may be fed into an intermediate vessel D in order to allow a postprecipitation of D,L-methionine. Finally, the D,L-methionine is isolated in a suitable solid/liquid separation step E, such as a filtration or centrifugation, whereupon the filtrate obtained can be fed back, if required, into the feed to apparatus A. This can lead to an enrichment of the additives according to the invention.

The examples which follow are intended to illustrate the invention in detail, but without restricting it.

EXAMPLES

Example 1

Anionic Surfactant Additive Screening 40 g of D,L-methionine and 360 g of water were charged in a flask and circulated via a heat exchanger by pumping at a temperature of 40° C. A solution of 125 g of D,L-methionine in 1125 g of water, heated to 90° C., was added to this suspension at a rate of 18 ml/min, wherein the temperature of the suspension charged was maintained at 40° C. After addition of 650 ml of the hot solution, 500 ml of suspension were removed and then a further 500 ml of the hot solution were added at a rate of 18 ml/min. The resulting suspension was drained off, the amount of foam determined in ml, and the D,L-methionine was filtered off and washed with 300 ml of acetone. After drying the D,L-methionine, the bulk density was determined.

For the experiments with $NH_3$, the desired concentration was calculated as $NH_4^+$ concentration and was adjusted in both start solutions/suspensions. Additionally, the amount of methionine was increased by an amount equimolar to the amount of added $NH_3$.

The crystallization experiments were carried out in the presence of the following additives, where the stated concentration was adjusted by addition of the additive in both start solutions/suspensions.

Additive 1

An aqueous mixture comprising 6.9% by weight of silicone oil with a kinematic viscosity of 1000 $mm^2$/s (AK 1000, Wacker-Chemie GmbH), 0.27% by weight of hydrophobized silica (Sipernat D10, Evonik Degussa GmbH) and 17.9% by weight of a polyethoxylated fatty acid mixture (Intrasol® FS 18/90/7, Ashland Deutschland GmbH) was used as pure defoamer 1 (additive 1, comparative example).

The pure crystallization additives used were the following anionic surfactants:

Additive 2) $C_nH_{2n+1}$—O—$SO_3Na$, where n=12 to 18 Sulfopon® 1218G, Oleochemicals)

Additive 3) $C_nH_{2n+1}$—O—$C_2H_4$—$SO_3Na$, where n=8 to 18 (Hostapon® SCI 85, Clariant)

Additive 4) $C_nH_{2n+1}$—$(OC_2H_4)_2$—O—$SO_3Na$, where n=12 (Disponil® FES 27, Cognis)

Comparative Example, additive 5) $C_nH_{2n+1}$—$(OC_2H_4)_{12}$—O—$SO_3Na$, where n=12 (Disponil® FES 993, Cognis)

Comparative Example, additive 6) $C_nH_{2n+1}$—$(OC_2H_4)_{30}$—O—$SO_3Na$, where n=12 (Disponil® FES 77, Cognis)

For the combination of the crystallization additives with a defoamer, an aqueous mixture 7 was used comprising 6.1% by weight of silicone oil with a kinematic viscosity of 1000 $mm^2$/s (AK 1000, Wacker Chemie GmbH), 0.25% by weight of hydrophobized silica (Sipernat D10, Evonik Degussa GmbH), 2.6% by weight of a polyethoxylated fatty acid mixture (Intrasole FS 18/90/7, Ashland Deutschland GmbH), 3.7% by weight of a polyethoxylated fatty alcohol mixture (2.35% by weight of Marlipal®, Sasol Germany GmbH, 1.35% by weight of Brij C2, Croda Chemicals Europe) in water (corresponds to 12.65% by weight of active ingredient).

This mixture was used in each case with 5.1% by weight of the corresponding crystallization additive (2, 3 or 4) in water (corresponds to 17.75% by weight of total active ingredient, made up to 100% by weight with water). The following additives were used:

Additive 8)=(7)+(2)
Additive 9)=(7)+(3)
Additive 10)=(7)+(4)

The ratio of defoamer 7:crystallization additive (2, 3, 4) was 2.5:1 (based on the active ingredient) in each case. The concentration data in Table 1 gives the total active ingredient content of the additive without water based on the total mass of the solution or suspension.

TABLE 1

| Additive | Additive concentration (ppm) [1] | $NH_4^+$ concentration (g/kg) [1] | Amount of foam (ml) | D,L-Methionine bulk density (g/l) |
|---|---|---|---|---|
| None | — | — | 550 | 453 |
| 1 (Comparative example) | 800 | 1 | 20-30 | 454 |
| 2 | 800 | 2.5 | 85 | 564 |
| 3 | 800 | 2.5 | 400 | 573 |
| 4 | 800 | 2.5 | 250 | 588 |
| 5 (Comparative example) | 800 | 2.5 | 800 | 492 |
| 6 (Comparative example) | 800 | 2.5 | 1000 | 463 |
| 8 | 800 | 2.5 | 0 | 630 |
| 9 | 800 | 2.5 | 0 | 634 |
| 10 | 800 | 2.5 | 20-30 | 630 |

[1] in the solution and/or suspension (analogously to Example 1)

Example 2

Influence of the $NH_4^+$ Concentration on the Bulk Density of Methionine 40 g of methionine and 360 g of water were charged in a flask and circulated via a heat exchanger by pumping at a temperature of 40° C. A solution of 125 g of methionine in 1125 g of water, heated to 90° C., was added to this suspension at a rate of 18 ml/min, wherein the temperature of the suspension charged was maintained at 40° C. After addition of 650 ml of the hot solution, 500 ml of suspension were removed and then a further 500 ml of the hot solution were added at a rate of 18 ml/mm. The resulting suspension was drained off, the amount of foam determined, and the methionine was filtered off and washed with 300 ml of acetone. After drying the methionine, the bulk density was determined.

For the experiments with $NH_3$, the desired concentration was calculated as $NH_4^+$ concentration and was adjusted in both start solutions/suspensions by addition of aqueous $NH_3$ solution.

The crystallization experiments were carried out in the presence of additive 8 (according to Example 1), wherein the stated concentration was adjusted by addition of the additive likewise in both start solutions/suspensions according to Table 2.

The concentration data in Table 2 give the total active ingredient content of the additive without water based on the total mass of the solution or suspension.

TABLE 2

| No. | Additive | Additive concentration (ppm)[1] | $NH_4^+$ concentration (g/kg)[1] | Amount of foam (ml) | D,L-Methionine bulk density (g/l) |
|---|---|---|---|---|---|
| 1 | None (comparison) | — | — | 350 | 434 |
| 2 | 8 (comparison) | 800 | — | 200 | 220 |
| 3 | 8 (comparison) | 800 | 0.25 | 0 | 420 |
| 4 | 8 (comparison) | 800 | 0.5 | 0 | 505 |
| 5 | 8 | 800 | 1 | 0 | 586 |
| 6 | 8 | 800 | 2.5 | 0 | 615 |

[1] in the solution and/or suspension (analogously to Example 1)

Example 3

Nonionic Surfactant 48 g of DI-methionine, 348 g of water and 3.8 g of aqueous $NH_3$ solution (25%) and 0.32 g of Tween 65 were charged in a flask and circulated via a heat exchanger by pumping at a temperature of 40° C. A solution of 151 g of D,L-methionine, 1087 g of water, 11.8 g of aqueous $NH_3$ solution (25%) and 1.0 g of Tween 65, heated to 90° C., was added to this suspension at a rate of 18 ml/min, wherein the temperature of the suspension charged was maintained at 40° C. After addition of 650 ml of the hot solution, 500 ml of suspension were removed and then a further 500 ml of the hot solution were added at a rate of 18 ml/min. The resulting suspension was drained off, the amount of foam determined, and the D,L-methionine was filtered off and washed with 300 ml of acetone. After drying the D,L-methionine, the bulk density was determined.

0 ml of foam occurred and the bulk density of the isolated D,L-methionine was 578 g/l.

Example 4

Concentration-Dependent Experiments 48 g of D,L-methionine, 348 g of water and 3.8 g of aqueous $NH_3$ solution (25%) were charged in a flask and circulated via a heat exchanger by pumping at a temperature of 40° C. A solution of 151 g of D,L-methionine, 1087 g of water and 11.8 g of aqueous $NH_3$ solution (25%), heated to 90° C., was added to this suspension at a rate of 18 ml/min, wherein the temperature of the suspension charged was maintained at 40° C. After addition of 650 ml of the hot solution, 500 ml of suspension were removed and then a further 500 ml of the hot solution were added at a rate of 18 ml/min. The resulting suspension was drained off, the amount of foam determined, and the D,L-methionine was filtered off and washed with 300 ml of acetone. After drying the D,L-methionine, the bulk density was determined.

The crystallization experiments were carried out in the presence of additives 8, 9 or 10 below (according to Example 1), wherein the stated concentration was adjusted by addition of the additive in both start solutions/suspensions according to Table 4.

Additive 8) (7)+(2)
Additive 9) (7)+(3)
Additive 10) (7)+(4)

The concentration data in Table 3 give the total active ingredient content of the additive without water based on the total mass of the solution or suspension.

TABLE 3

| No. | Additive | Additive concentration (ppm)[1] | Amount of foam (ml) | D,L-Methionine bulk density (g/l) |
|---|---|---|---|---|
| 1 | 8 | 100 | 350 | 522 |
| 2 | 8 | 200 | 180 | 561 |
| 3 | 8 | 400 | 5 | 610 |
| 4 | 8 | 800 | 0 | 630 |
| 5 | 8 | 1200 | 0 | 624 |
| 6 | 8 | 2000 | 0 | 615 |
| 7 | 8 | 4000 | 0 | 616 |
| 8 | 9 | 100 | 450-500 | 529 |
| 9 | 9 | 200 | 200 | 585 |
| 10 | 9 | 400 | 20-30 | 625 |
| 11 | 9 | 800 | 0 | 634 |
| 12 | 9 | 1200 | 0 | 657 |
| 13 | 9 | 2000 | 0 | 630 |
| 14 | 9 | 4000 | 0 | 601 |
| 15 | 10 | 100 | 350 | 507 |
| 16 | 10 | 200 | 150 | 558 |
| 17 | 10 | 400 | 80 | 614 |
| 18 | 10 | 800 | 20-30 | 630 |
| 19 | 10 | 1200 | 20-30 | 652 |
| 20 | 10 | 2000 | 5-10 | 650 |
| 21 | 10 | 4000 | 0 | 636 |

[1] in the solution and/or suspension (analogously to Example 1)

It can be seen that the additives according to the invention (with defoamer) over the concentration range of 400 to 4000 ppm improve the bulk density of the D,L-methionine to values >600 g/l.

The invention claimed is:
1. A method comprising crystallizing D,L-methionine from an aqueous solution and/or suspension comprising D,L-methionine and D,L-methionine ammonium salt, having a Met content of 70-180 g/kg of solution and/or suspension, an $NH_4^+$ content of 1-5 g/kg of solution and/or suspension, in the presence of a crystallization additive, which comprises a nonionic or anionic surfactant,
  wherein a temperature of the solution and/or suspension is lowered directly or stepwise from $T_1=85-110°$ C. to $T_2=30-50°$ C., so that D,L-methionine precipitates as a solid.

2. The method of claim 1, wherein the crystallization additive comprises at least one anionic surfactant selected from the group consisting of a compound depicted in formulae 1 to 3:

$$R^1-O-SO_3M \quad \text{(formula 1)}$$

$$R^2-O-(CH_2)_n-SO_3M \quad \text{(formula 2)}$$

$$R^3-(OC_2H_4)_n-O-SO_3M \quad \text{(formula 3)}$$

wherein n is an integer from 1 to 10, M is sodium or potassium and $R^1$, $R^2$ and $R^3$ are a linear, branched or cyclic, saturated or unsaturated $C_8$- to $C_{20}$-alkyl group or an aryl group.

3. The method of claim 2, wherein n is equal to 2 and $R^1$, $R^2$ and $R^3$ are linear, saturated $C_8$- to $C_{18}$-alkyl groups.

4. The method of claim 2, wherein the anionic surfactant comprises
$C_nH_{2n+1}-O-SO_3Na$, where n=12 to 18,
$C_nH_{2n+1}-O-C_2H_4-SO_3Na$, where n=8 to 18, or
$C_nH_{2n+1}-(OC_2H_4)_2-O-SO_3Na$, where n=12.

5. The method of claim 1, wherein the crystallization additive comprises a nonionic surfactant that is a sorbitan fatty acid ester or a mixture of sorbitan fatty acid esters.

6. The method of claim 5, wherein the sorbitan fatty acid ester has a formula (4)

wherein w+x+y+z=20.

7. The method of claim 1, wherein a concentration of the crystallization additive in the solution and/or suspension from which the crystallization takes place is at least 700 ppm and not more than 4000 ppm, based on the total mass of the solution and/or suspension.

8. The method of claim 1, wherein the solution from which the crystallization takes place further comprises a defoamer.

9. The method of claim 8, wherein the defoamer comprises silicone oil.

10. The method of claim 8, weight ratio of defoamer: crystallization additive, based on an active ingredient, is in a range of 4:1 to 1:1, and the concentration of the crystallization additive is at least 50 ppm and not more than 1200 ppm, based on the total mass of the solution and/or suspension.

11. The method of claim 1, wherein the crystallization takes place by introducing an aqueous solution and/or suspension comprising D,L-methionine and D,L-methionine ammonium salt heated to 85 to 110° C. into an aqueous solution and/or suspension comprising D,L-methionine and D,L-methionine ammonium salt warmed to 30 to 50° C., wherein a temperature of the resulting mixture is constantly maintained between 30 and 50° C.

12. The method of claim 11, wherein the crystallization takes place by introducing a solution comprising D,L-methionine and D,L-methionine ammonium salt heated to 85 to 110° C. into a suspension comprising D,L-methionine and D,L-methionine ammonium salt warmed to 30 to 50° C.

13. The method of claim 1, wherein the crystallization is carried out in two stages, wherein, in a first crystallization stage, a solution and/or suspension comprising D,L-methionine and D,L-methionine ammonium salt heated to 85 to 110° C. is introduced into a suspension comprising D,L-methionine and D,L-methionine ammonium salt warmed to 60 to 80° C. and a temperature of the resulting mixture is constantly maintained between 60 and 80° C. and wherein the suspension comprising D,L-methionine and D,L-methionine ammonium salt warmed to 60 to 80° C. obtained in the first crystallization stage is introduced in a second crystallization stage into a suspension comprising D,L-methionine and D,L-methionine ammonium salt warmed to 30 to 50° C., wherein a temperature of the resulting mixture is constantly maintained between 30 and 50° C.

14. The method of claim 1, wherein the crystallization is carried out by vacuum crystallization, wherein a pressure in the crystallization stage is 60 to 1000 mbar and, if a two-stage crystallization is carried out, a pressure in the second crystallization stage is 35 to 200 mbar.

15. The method of claim 1, wherein the aqueous solution and/or suspension comprising D,L-methionine and D,L-methionine ammonium salts were prepared beforehand by dissolving and/or suspending D,L-methionine in water in the presence of an appropriate amount of ammonia.

16. The method of claim 15, wherein D,L-methionine having a methionine content of at least 90% by weight is used for the dissolution.

17. The method of claim 16, wherein D,L-methionine is present in a form of pure methionine and/or crude methionine from a manufacturing process, having a residual moisture of 0.1 to 9.5% by weight.

18. A method for preparing D,L-methionine, comprising:
  forming an aqueous solution of D,L-methionine ammonium salt by hydrolysis of D,L-methionine nitrile and/or D,L-methionine amide,
  partially removing ammonia from the D,L-methionine ammonium salt, to obtain an aqueous solution and/or suspension containing comprising D,L-methionine and D,L-methionine ammonium salt, and
  producing methionine by crystallization by performing the method of claim 1.

19. The method of claim 18, wherein the aqueous solution of D,L-methionine ammonium salt is brought to an $NH_4^+$ content of 1-5 g/kg of solution and/or suspension by evaporating and/or stripping off of ammonia prior to the crystallization.

20. The method of claim 18, wherein the aqueous solution and/or suspension of D,L-methionine and D,L-methionine ammonium salt is brought to a Met content of 70-180 g/kg of solution and/or suspension by addition of water and/or D,L-methionine.

21. The method of claim 1, wherein the precipitated D,L-methionine is separated from the mother liquor and dried or is initially recrystallized and is dried after separation from the mother liquor obtained.

22. The method of claim 21, wherein the mother liquor is fed back into a crystallization stage.

* * * * *